United States Patent
Bialleck et al.

(10) Patent No.: US 12,286,394 B2
(45) Date of Patent: *Apr. 29, 2025

(54) CRYSTALLINE FORM OF TREOSULFAN

(71) Applicant: Medac Gesellschaft Für Klinische Spezialpräparate MBH, Wedel (DE)

(72) Inventors: Sebastian Bialleck, Wedel (DE); Sven Haferkamp, Mönchengladbach (DE); Anna Mellor, Hamburg (DE); Dominique Anna Gopalakrishnan, Mülheim an der Ruhr (DE); Jürgen Dworak, Bochum (DE)

(73) Assignee: Medac Gesellschaft Für Klinische Spezialpraparate MBH, Wedel (DE)

( * ) Notice: Subject to any disclaimer, the term of this patent is extended or adjusted under 35 U.S.C. 154(b) by 1070 days.

This patent is subject to a terminal disclaimer.

(21) Appl. No.: 17/279,157

(22) PCT Filed: Sep. 25, 2019

(86) PCT No.: PCT/EP2019/075828
§ 371 (c)(1),
(2) Date: Mar. 24, 2021

(87) PCT Pub. No.: WO2020/064815
PCT Pub. Date: Apr. 2, 2020

(65) Prior Publication Data
US 2021/0387945 A1 Dec. 16, 2021

(30) Foreign Application Priority Data
Sep. 26, 2018 (EP) ..................... 18196966

(51) Int. Cl.
*C07C 309/66* (2006.01)
*A61K 9/19* (2006.01)

(52) U.S. Cl.
CPC .............. *C07C 309/66* (2013.01); *A61K 9/19* (2013.01); *C07B 2200/13* (2013.01)

(58) Field of Classification Search
CPC .................................................. C07C 309/66
See application file for complete search history.

(56) References Cited

U.S. PATENT DOCUMENTS

| | | |
|---|---|---|
| 6,684,524 B1 | 2/2004 | Sennhenn et al. |
| 7,199,162 B1 | 4/2007 | Baumgart |

FOREIGN PATENT DOCUMENTS

| | | |
|---|---|---|
| DE | 1188583 | 3/1965 |
| DE | 1193938 | 6/1965 |
| EP | 1227808 | 8/2002 |

(Continued)

OTHER PUBLICATIONS

Treosulfan Package Leaflet, Medac Gesellschaft fur klinische Spezialpraparate, Apr. 2017 (Year: 2017).*

(Continued)

*Primary Examiner* — Matthew P Coughlin
(74) *Attorney, Agent, or Firm* — Hovey Williams LLP; Crissa A. Cook

(57) ABSTRACT

A crystalline form of treosulfan and methods to prepare it are described. This crystalline form of treosulfan is useful in pharmaceutical compositions for the treatment of cancer and for conditioning therapy before transplantation of bone marrow or blood stem cells.

19 Claims, 5 Drawing Sheets

(56) References Cited

FOREIGN PATENT DOCUMENTS

| EP | 2599484 | 6/2013 |
|---|---|---|
| GB | 896052 | 5/1961 |
| GB | 891466 | 3/1962 |
| JP | 200350665 | 2/2003 |
| JP | 2009526199 | 12/2012 |
| WO | 2007095033 | 8/2007 |
| WO | 2014127802 | 8/2014 |
| WO | 2015107534 | 7/2015 |

OTHER PUBLICATIONS

Gropp et al. Gynecologic Oncology 1998, 71, 94-98 (Year: 1998).*
Casper et al. Blood, 2004, 103, 725-731 (Year: 2004).*
International Search Report and Written Opinion in corresponding PCT/EP2019/075828, dated Nov. 13, 2019.
Robbins, et al., "Synthesis of Chiral Non-Racemic Diols From (S,S>-1,2,3,4-Diepoxyrütäne: (2S3S)-DffiYBRÖXY-I,4" Difhenylbutane", Orgaric Syntheses, 76, Jan. 1, 1999, p. 101.
Feit, "1,4-Bismetlianesulfoiiates of the Stereoisomeric Butanetetraols and Related Compounds", J Medicinal Chemistry, 7(1), Jan. 1, 1964, pp. 14-17.
Baynes et al., "A phase 1 trial of escalating treosulfan in combination with high-dose melphalan and decarbazine (TMD) with peripheral blood progenitor cell transplant (PBPCT) in recurrent metastatic ovarian and breast cancer", Blood, 96(11), 2000.
Von Pawel, et al. "Clinical Phase II Trial of Treosulfan in Patients with Non-Resectable Non-Small-Cell Lung Cancer", Onkologie, 21, 1998, pp. 316-319.
International Preliminary Report on Patentability in corresponding PCT/EP2019/075828, dated Mar. 23, 2021.
Chekerov, et al., "Treosulfan in the Treatment of Advanced Ovarian Cancer-Results of a German Multicenter Non-Interventional Study", Anticancer Research, 2015, 35, pp. 6869-6876.
Slatter, et al., "Treosulfan and Fludarabine Conditioning for Heniatopoietic Stern Cell Transplantation in Children with Primary Immunodefidency: UK Experience", Blol Blood Marrow Transplant, 2018, 24, pp. 529-536.

Notice of Reasons for Refusal in corresponding Japanese Patent Application Serial No. 2021-516734, dated Oct. 5, 2022 (English machine translation attached).
Notice of Reasons for Refusal in corresponding Japanese Patent Application Serial No. 2021-516733, dated Oct. 19, 2022 (English machine translation attached).
Experimental Chemistry Course (Sequel), 2. Separation and Purification, Maruzen Inc., Jan. 25, 1967, pp. 159-178 and 186-187.
Ashizawa, et al., "Polymorphism and crystallization of the pharmaceutical drugs", Japan, Maruzen Planet Co., Ltd, 2002, pp. 3-16 and 273-278.
Takada, et al., "Drug Form screening and selection in the drug development phase", Pharm Stage, 2007, 10(6), pp. 20-25.
Yamano, et al., "Approach to Crystal Polymorph in Process Research of New Drug", Journal of Synthetic Organic Chemistry Japan, 2007, 65(9), pp. 907-913.
Mangin, et al., "Polymorphism in Processes of Crystallization in Solution: A Practical Review", Org. Process Res. Dev., 2009, 13(6), pp. 1241-1253.
The Japanese Pharmacopoeia, 16th Edition, 2011, p. 64-68 and 2070.
Kawakami, et al., "Formulation technology using amorphous state", Farumashia, 2016, 52(5), p. 402.
FDA, Guide to Inspections of Lyophilization of Parenterals [Japanese/English], Jun. 1993, retrieved from: https://www.ph-s.com/uploads/technical_documents/2009/06/tech200906_7.pdf.
Yonemochi, "Effects of formulation factors on the crystal structure of freeze dried sugar alcohols", The Proceedings of Hoshi University, 2016, 201, 57, 1-9, (English abstract attached).
Office Action in corresponding Japanese Patent Application Serial No. 2021-516733, dated Apr. 24, 2023 (English translation attached).
Pre-Appeal Examination Report in corresponding Japanese Patent Application Serial No. 2021-516733, dated Nov. 9, 2023 (English translation attached).
Farumashia, "Table of contents/Special feature/Cover explanation", The Pharmaceutical Society of Japan, 2016, 52(5), pp. 374-375 (English abstract attached).

* cited by examiner

CRYSTALLINE FORM OF TREOSULFAN

RELATED APPLICATIONS

This application is the U.S. National Stage of International Patent Application No. PCT/EP2019/075828, filed Sep. 25, 2019, which is hereby incorporated by reference in its entirety, and which claims priority to European Patent Application No. 18196966.8, filed Sep. 26, 2018.

The invention relates to a new crystalline form of treosulfan, designated as crystalline form B of treosulfan, which has favourable characteristics for use as a pharmaceutically active ingredient and for the preparation of corresponding pharmaceutical compositions.

Treosulfan, chemical name (2S,3S)-(−)1,4-di(mesyloxy)-2,3-butanediol or L-Threitol-1,4-di(methanesulfonate), has the following chemical formula:

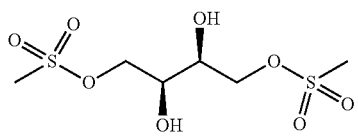 [SMILES: CS(=O)(=O)OC[C@H](O)[C@@H](O)COS(C)(=O)=O]

The chemical synthesis of treosulfan has been disclosed in DE 188 583 and DE 1 193 938 and is for example effected by reacting L-1,4-dibromobutane-2,3-diol and the silver salt of methanesulfonic acid.

Treosulfan is a dihydroxy derivative of busulfan and acts as an antineoplastic agent in view of its ability to alkylate the DNA. It is in use for the treatment of ovarian cancer either as such or in combination with further chemotherapeutics for example melphalan and dacarbazine (Baynes et al., Blood 96(11): 170a, Abstr. No. 731, 2000). For the treatment of ovarian cancer the monotherapy with treosulfan involves administering to the patient an amount of 8 g/m$^2$ body surface area, whereas the combination therapy with treosulfan and cisplatin involves administering treosulfan in an amount of 5 g/m$^2$.

Treosulfan has also been used in the treatment of advanced, non resectable non-small cell lung carcinomas (Pawel et al., Onkologie 21:316-319; 1998).

Furthermore, EP 1 227 808 A1 discloses the use of treosulfan in conditioning therapy before bone marrow or blood stem cell transplantation to a patient. In such conditioning therapy, the administration of treosulfan can effectively be combined with either administration of further agents, e.g. cyclophosphamid, carboplatin, thiotepa, melphalan, fludarabin, immune suppressive antibodies, or irradiation of the body. In comparison to the use of busulfan, serious side effects can predominantly or entirely be avoided. High dosages of treosulfan can even be used without causing serious liver, lung, kidney or CNS toxicities. The conditioning phase comprises a period of 2 to 7 days with a total dose of treosulfan of at least 20 g/m$^2$ body surface area before allogenic transplantation of bone marrow or haematopoietic stem cells.

Treosulfan is commercially available as capsules for oral use and a sterile powder consisting of treosulfan for preparing a solution for infusion. The solution is administered intravenously within about 15 to 30 minutes. The treosulfan in these products is a crystalline form exhibiting a powder X-ray diffraction (XRPD) pattern having characteristic peaks at 7.69, 15.43, 18.74, 19.14, 19.77, 20.15, 20.28, 21.24, 21.74, 22.07, 22.96, 23.24, 24.36, 25.29, 28.05, 28.28, 28.97, 30.10 and 40.55±0.2 degrees 2Θ. This crystalline form is in the following designated as form A and its XRPD pattern is shown in FIG. 3.

For preparing a solution for infusion, the commercial sterile powder is dissolved in e.g. water to a concentration of 50 mg/ml and the obtained solution is diluted with e.g. isotonic NaCl solution. However, the water used as solvent has to be warmed to 30° C. for the reconstitution step. Moreover, the powder has to be completely removed from the walls of the vial. This step is important to avoid formation of powder particles which are sticking to the wall. Such sticky particles of form A of treosulfan are difficult to be dissolved and they protract the complete dissolution. The whole process for preparing a solution for infusion from the sterile powder, including the preparation of the vial, the necessary warming of water and the complete dissolution of the powder, takes about 10 minutes. Moreover, the use of warm solvent enhances the risk of undesired degradation.

WO 2015/107534 refers to two allegedly novel and distinct polymorphic forms of treosulfan, designated as form I and form II. The document lacks any indication whatsoever as to how form II can be obtained and hence lacks enabling disclosure for form II. The process for preparing form I is described only in a very general manner and is said to merely involve recrystallisation from organic solvents or mixtures thereof with some preferred organic solvents being mentioned. No disclosure of a specific process to prepare form I is provided. The x-ray powder diffraction pattern given for form I strongly resembles that of the crystalline form A of the commercially available product which is represented in FIG. 3 below suggesting these forms to be actually identical. Finally, WO 2015/107534 also describes lyophilized formulations which are said to typically include treosulfan of form I.

The known crystalline forms of treosulfan, however, suffer from a couple of further disadvantages.

In particular, the known forms have a tendency to form agglomerates. This is highly undesirable as agglomerates can lead to unpredictable and highly variable dissolution behaviour. Moreover, agglomerates lead to problems in achieving the desired even distribution of treosulfan in the final pharmaceutical composition to be administered to the patient. This can have a severe impact on the content uniformity of the pharmaceutical composition which in turn affects its efficacy and safety to the patient. In addition, the general tendency to form agglomerates may upon storage result in particularly high amounts thereof which is very undesirable. The tendency to form agglomerates also leads to a heterogeneous particle size distribution which affects the processing of the known crystalline forms to the desired final pharmaceutical compositions.

The lyophilized formulations of known crystal forms as are disclosed in WO 2015/107534 also suffer from drawbacks with regard to the long times required for their reconstitution as well as the presence of high amounts of methanesulfonic acid and water, in particular upon storage, and hence their stability. Methanesulfonic acid is a degradation product of treosulfan. Due to its strong acidity it accelerates hydrolysis of the ester groups of treosulfan and thus enhances the degradation process. For this reason the amount of methanesulfonic acid should be as low as possible.

It is, therefore, an object of the present invention to provide a form of treosulfan which avoids the disadvantages of the known crystalline forms of treosulfan.

This object is achieved by the crystalline form B of treosulfan according to claims 1 to 4.

The invention also relates to the treosulfan according to claims 5 to 8, the process according to claims 9 to 13, the pharmaceutical compositions according to claims 14 to 15, the crystalline form B of treosulfan for use in medicine according to claims 16 to 18 and the use according to claim 19.

DETAILED DESCRIPTION

The crystalline form B of treosulfan according to the invention is exhibiting an X-ray powder diffraction pattern having peaks at 20.87 and 23.47±0.20 degrees 2Θ and in particular at 20.87, 23.47, 26.20, 29.65, 30.81, 34.54, 35.30, 36.87 and 46.24±0.20 degrees 2Θ.

Figure 1:
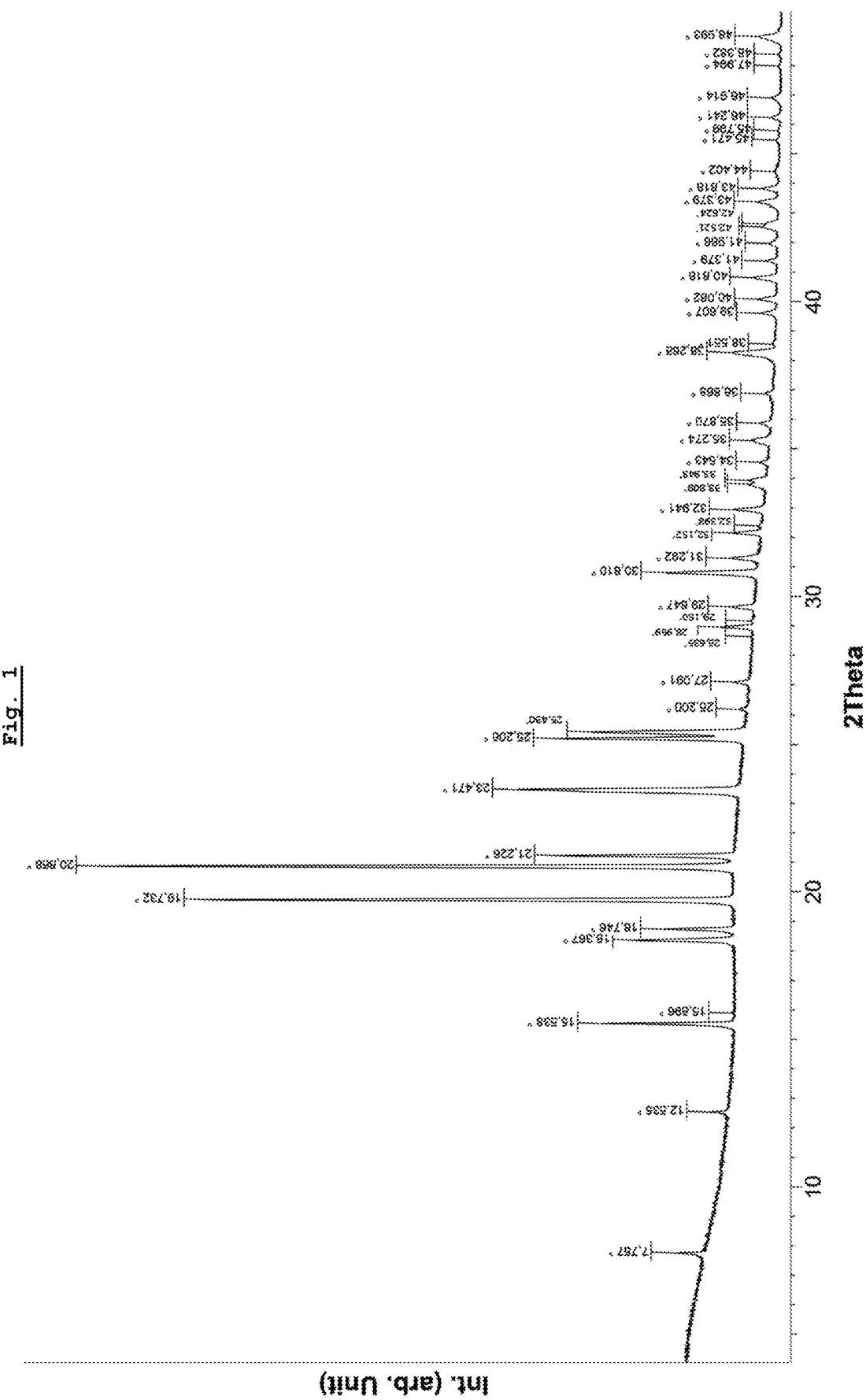
FIG. 1 shows an XRPD pattern of crystals of crystalline form B of treosulfan.

The crystalline form B according to the invention is in particular characterized by exhibiting an X-ray powder diffraction pattern essentially as shown in FIG. 1.

In a further preferred embodiment, the crystalline form B according to the invention is exhibiting an X-ray powder diffraction pattern having no peaks in at least one, and preferably in all of the following regions a to f, expressed as degrees 2Θ:

| Region | Degrees 2Θ |
| --- | --- |
| a | 19.00-19.50 |
| b | 20.00-20.65 |
| c | 21.50-23.21 |
| d | 23.75-24.95 |
| e | 27.40-28.35 |
| f | 30.00-30.60 |

The crystalline form B according to the invention is preferably also characterized by the space group and the parameters a, b, c, α, β, γ of the unit cell as well as the volume of the unit cell obtained by single-crystal x-ray diffraction (SCXRD) analysis, which structural data are given in the following table together with further information especially on the quality of the fit in comparison to those of the commercial form A.

|  | Form A | Form B (Invention) |
| --- | --- | --- |
| Space group | orthorhombic, $P2_12_12_1$ | monoclinic, $P2_1$ |
| a | 5.5306(5) Å | 5.5692(9) Å |
| b | 8.9220(8) Å | 8.9469(15) Å |
| c | 22.8442(18) Å | 11.322(2) Å |
| α | 90° | 90° |
| β | 90° | 95.497 (16)° |
| γ | 90° | 90° |
| V | 1127.22(17) Å³ | 561.54(17) Å³ |
| Z/Z' | 4/1 | 2/1 |
| Final R indices | R1 = 0.0256, | R1 = 0.0798, |
| (observed data, I > 2σ(I)) | wR2 = 0.0462 | wR2 = 0.1956 |
| R indices | R1 = 0.0280, | R1 = 0.0912, |
| (all data) | wR2 = 0.0471 | wR2 = 0.2065 |
| Goodness of fit | 0.966 | 1.163 |
| T | 173(2) K | 173(2) K | a, b and c=Lengths of edges of unit cell
α, β and γ=Angles between edges of unit cell
V=Volume of unit cell
Z/Z'=Number of molecules in unit cell
R1 and wR2=Confidence values
T=Temperature at which analysis has been carried out As can be seen from these data, form B has two molecules per unit cell (space group $P2_1$) and a volume of 561.5 Å³, whereas form A has four molecules per unit cell (space group $P2_12_12_1$) and a volume of 1127.22 Å³.

The invention also relates to treosulfan which comprises at least 96% by weight, in particular at least 97% by weight, preferably at least 98% by weight and more preferably at least % by weight of the crystalline form B according to the invention, relative to the combined amount of crystalline form B and crystalline form A.

The treosulfan according to the invention, therefore, comprises only very small amounts of the conventional crystalline form A and very high amounts of the crystalline form B of the invention. The high polymorphic purity is particularly advantageous for the use of the treosulfan of the invention in particular as active ingredient of pharmaceutical compositions.

The invention also relates to treosulfan which comprises at least 75% by weight, in particular at least 80% by weight, preferably at least 85% by weight, more preferably at least 90% by weight and even more preferably at least 95% by weight of the crystalline form B, relative to the amount of treosulfan.

In a preferred embodiment the treosulfan according to the invention comprises less than 20% by weight, in particular less than 15% by weight, preferably less than 10% by weight and more preferably less than 5% by weight of amorphous phase, relative to the amount of treosulfan.

The small amount of amorphous phase avoids a couple of significant disadvantages associated with this phase. First of all, the amorphous phase tends to result in uncontrolled crystallization. In addition, it is more quickly degraded, has a higher residual moisture content after drying, shows inferior flowability and wettability and more easily becomes electrostatically charged. All of these properties are not desirable for a pharmaceutically active ingredient.

In a further preferred embodiment the treosulfan according to the invention comprises less than 0.2% by weight, preferably less than 0.1% and more preferably less than 0.05% by weight of methanesulfonic acid. The particularly small amount of methanesulfonic acid is one reasonable explanation for the high storage stability of the treosulfan of the invention as this acid accelerates hydrolysis of the ester groups of treosulfan and therefore promotes its degradation.

It has surprisingly been found that the crystalline form B according to the invention and the treosulfan according to the invention show in addition to the advantages mentioned above also further favorable characteristics for use as a pharmaceutically active ingredient and for the preparation of corresponding pharmaceutical compositions.

Figure 2:
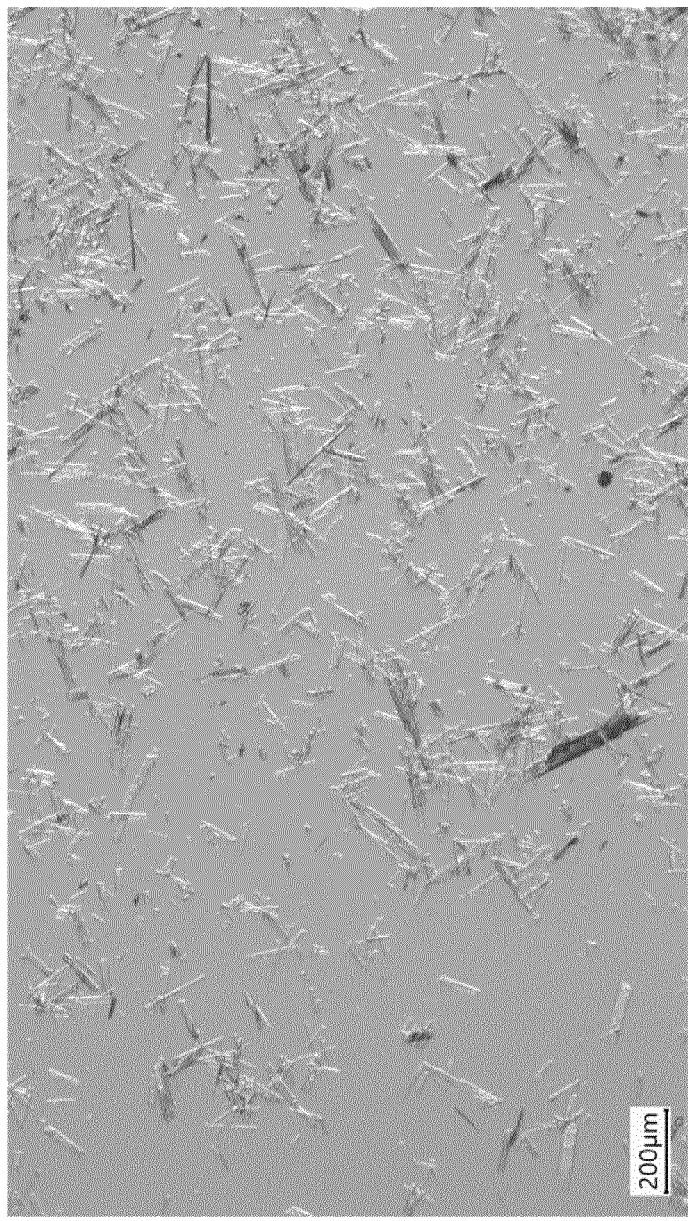
FIG. 2 shows a photomicrograph of crystals of crystalline form B of treosulfan.
Figure 4:
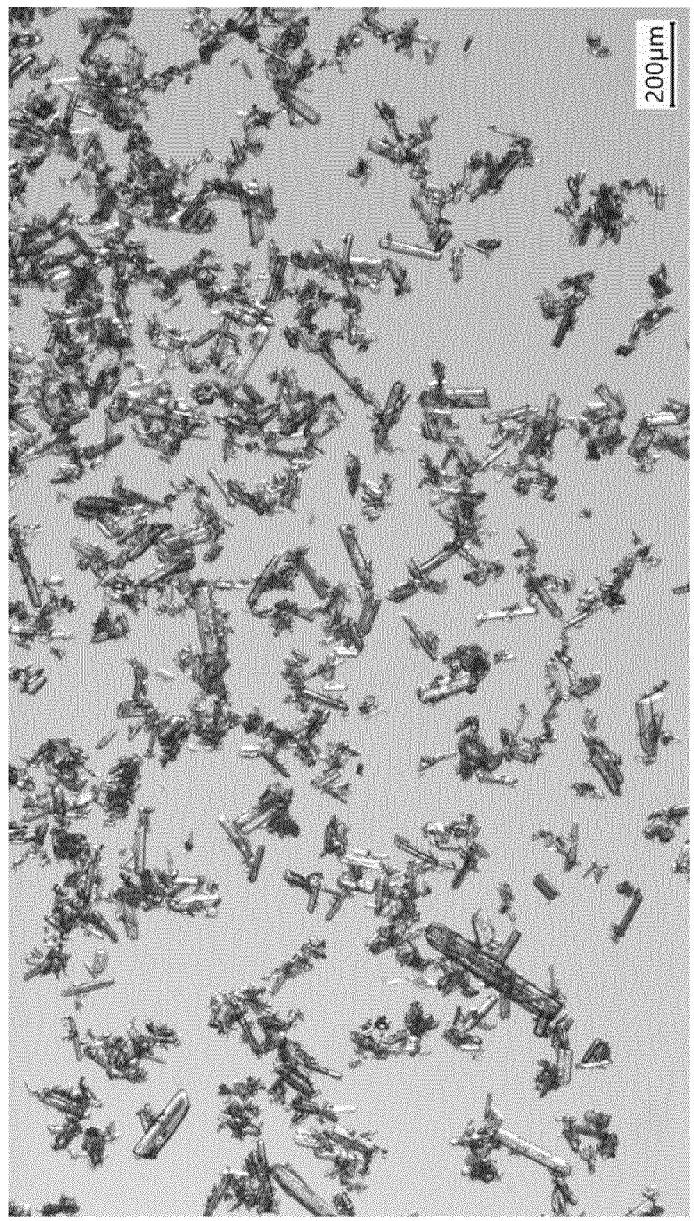
FIG. 4 shows a photomicrograph of crystals of crystalline form A of treosulfan.

In particular, it has been found that the crystalline form B has an advantageous particle size distribution. In contrast to the commercial form A, form B according to the invention has a much smaller tendency to form agglomerates of particles. This has been shown by investigations using an optical microscope and the corresponding photomicrographs for form B and form A are represented in FIGS. 2 and 4, respectively. They show that the particle size distribution of form B is significantly narrower which in particular leads to a high uniformity of the content of the active ingredient treosulfan in corresponding pharmaceutical compositions.

Moreover, as can be seen from the photomicrographs the crystals of form B are long thin blade-like crystallites, whereas crystals of form A are long columnar crystals. The blade-like crystals of form B have a much higher surface to volume ratio in comparison to the long columnar crystals of form A.

The invention also relates to a process for preparing the crystalline form B of treosulfan and the treosulfan according to the invention. The process comprises
- (A) recrystallizing treosulfan from organic solvent, optionally comprising water, or
- (B) dissolving treosulfan in organic solvent, optionally comprising water, and allowing evaporation of solvent and optional water to dryness, in particular at room temperature, or
- (C) dissolving treosulfan in organic solvent, optionally comprising water, and adding an anti-solvent.

The treosulfan used in the process according to the invention can be of any form and in particular is the commercially available form A of treosulfan.

The organic solvent in variant (A), variant (B) and variant (C) is in particular selected from the group of ethers, ketones, esters and alcohols or mixtures thereof and is preferably dioxane, methyl isobutyl ketone, ethyl acetate, tetrahydrofuran, and isopropanol or a mixture thereof.

In variant (A) the recrystallizing of treosulfan is typically effected by dissolving it in the selected organic solvent, which may include water, filtering the obtained solution, causing crystallization by keeping the solution at a reduced temperature of e.g. about 0° C. for some time and separating the crystals formed by filtration.

In variant (B), the room temperature is usually between 20 and 25° C. In a preferred embodiment, evaporation is effected at room temperature and at an ambient pressure of about 1 bar. This is typically effected by leaving the solution in an open container thereby allowing evaporation of solvent and optional water to take place until a dry product is obtained.

In another preferred embodiment of variant (B), a mixture of water and isopropanol is used and water and isopropanol are allowed to evaporate to dryness at room temperature. The mixture has preferably a temperature of about 65° C. It is also particularly preferred that the mixture comprises about 80% by weight of water and about 20% by weight of isopropanol.

Typically, this preferred embodiment of variant (B) involves placing treosulfan in a first container, such as a vial, adding a mixture of water and isopropanol, and transferring the obtained solution through a filter into another container, such as a vial, which is left open at room temperature to allow evaporation of water and isopropanol. It is preferred that the mixture, any equipment used for transferring and filtering the solution as well as the second container have been heated to a temperature of about 65° C.

In a preferred embodiment of variant (C), the anti-solvent is selected from methyl tert-butyl ether, toluene, hexane, pentane, chloroform, and methylene chloride.

Variant (C) is typically effected by dissolving treosulfan in the selected organic solvent, which may include water, filtering the obtained solution, adding the solution to the anti-solvent to cause crystallization and separating the crystals formed by filtration.

The invention also relates to a pharmaceutical composition comprising the crystalline form B according to the invention or the treosulfan according to the invention and optionally at least one pharmaceutically acceptable additive.

Pharmaceutically acceptable additives include e.g. fillers, binders, carriers, diluents, disintegrants, lubricants, stabilizers, buffering agents, emulsifiers, sweeteners, flavoring agents, preserving agents and moistening agents.

Depending on the mode of administration, the pharmaceutical composition according to the invention may comprise 0.01 to 100% by weight, 1 to 90% by weight, 25 to 80% by weight, 30 to 70% by weight, 40 to 60% by weight or about 50 wt.-% of the crystalline form B or the treosulfan according to the invention.

Pharmaceutical compositions may be for systemic administration, e.g. oral administration in the form of tablets, micro tablets, granules, powders, capsules, syrups, or multi-unit pellets, pills, pastilles, sachets or solutions, or for parenteral administration, e.g. intravenous, subcutaneous or intra-articular, in the form of solutions, suspensions or emulsions, which may be formed from powders or lyophilisates, or for rectal administration in the form of suppositories, foams or the like.

Additives for tablets are preferably selected from the group consisting of fillers, binders, disintegrants, and lubricants. Examples of fillers are polyols or sugars, with preferred fillers being selected from the group of mannitol, saccharose, sorbitol, starch, maltose, glucose, lactose, dextrose, xylitol and cellulose derivatives. Examples of lubricants are magnesium stearate, calcium stearate, talcum or polyethylene glycols. Further suitable additives for tablets are selected from the group of starch, gum, calcium silicate, microcrystalline cellulose, polyvinylpyrrolidone, sugar or cellulose-derivatives. Further examples of additives for tablets are buffers such as phosphate, citrate, tartrate and/or succinate buffers as stabilizers or pH controlling agents, and additives facilitating formation of granules.

The pharmaceutical composition according to the invention may take the form of a compressed tablet which is optionally coated with one or more film forming agents. In particular, the tablet coating may comprise at least one component selected from the group of cellulose derivatives, e.g. pre-gelatinized starch, cellulose ether (e.g. ethyl cellulose, methyl cellulose, hydroxyethyl cellulose and hydroxypropyl cellulose, in particular cross-linked sodium carboxymethyl cellulose), cellulose esters (e.g. cellulose acetate phthalate or hydroxypropyl methylcellulose phthalate), acrylic polymers or copolymers, preferably methacrylate aminoester copolymers (e.g. Eudragit RS or Eudragit RL), or methacrylic acid ethyl acrylate copolymers (e.g. methacrylic acid ethyl acrylate copolymer 1:1), waxy materials (e.g. carnauba wax), polyethylene glycols (e.g. Macrogol 6,000, Macrogol 20,000), (cross-linked) polyvinyl pyrrolidone (e.g. Povidon K30, Povidon K25, Crospovidon), polyvinyl alcohol or derivatives thereof (e.g. polyvinyl acetate phthalate), pigments (e.g. titanium dioxide), stearic acid, magnesium stearate, glycerol mono stearate and talcum.

The pharmaceutical composition according to the invention may also take the form of a liquid preparation for oral administration, e.g. a syrup or suspension. Examples of additives included in such a liquid preparation are sugar and/or a mixture of ethanol, water, glycerol and propylene glycol, preferably buffered to a suitable pH value. The liquid preparation may preferably also include at least one additive selected from the group of colouring agents, flavouring agents, saccharine and/or carboxmethyl cellulose as a thickening agent.

Moreover, the pharmaceutical composition according to the invention may also take the form of a hard or a soft capsule, wherein the crystalline form B or the treosulfan according to the invention may be admixed with a vegetable oil or polyethylene glycol. Hard capsules may also be filled with liquid or semisolid compositions containing the crystalline form B or the treosulfan according to the invention.

Pharmaceutical compositions according to the invention for parenteral use are sterile, aqueous or non-aqueous compositions. They typically include at least one aqueous and/or non-aqueous solvent. Usually, parenteral compositions are isotonic or are diluted with isotonic dilution means, e.g. isotonic NaCl solution.

Pharmaceutical compositions according to the invention in form of solutions for injection or infusion or suspensions may be prepared from sterile powders, lyophilisates, granules, and/or tablets which may be present in unit-dose or multi-dose containers, for example, sealed ampoules and vials. The compositions may include antioxidants, buffering agents or surfactants. Aqueous and non-aqueous suspensions may include suspending agents and thickening agents.

It is preferred that the pharmaceutical composition according to the invention is in form of a powder, a tablet, granules, or a capsule and in particular in form of a lyophilisate.

It has surprisingly been found that a lyophilisate according to the invention including the crystalline form B or the treosulfan according to the invention shows very favorable characteristics and in particular contains only a very small amount of methanesulfonic acid even after storage. In addition, such lyophilisate exhibits also a superior reconstitution behavior as the time necessary for its complete dissolution is typically only 90 seconds or even less. This is a substantial advantage in comparison to the conventional products when preparing ready-to-use solutions, e.g. solutions for infusion or injection, from the lyophilisate.

The invention also relates to crystalline form B, the treosulfan or the pharmaceutical composition according to the invention for use as a medicament. In a further embodiment, the invention also relates to crystalline form B, the treosulfan or the pharmaceutical composition according to the invention for use in the treatment of cancer and in particular ovarian cancer. In yet another embodiment, the invention also relates to crystalline form B, the treosulfan or the pharmaceutical composition according to the invention for use in conditioning therapy before transplantation of bone marrow or of blood stem cells.

In a further aspect, the invention also relates to the use of the crystalline form B, the treosulfan or the pharmaceutical composition according to the invention for treatment of cancer or for conditioning therapy before bone marrow or blood stem cell transplantation.

In a further aspect, the invention also relates to a method of treating patients suffering from cancer or a method of conditioning patients before marrow or blood stem cell transplantation, which methods involve administering to the patients the crystalline form B, the treosulfan or the pharmaceutical composition according to the invention.

Finally, the invention also relates to the use of the crystalline form B, the treosulfan or the pharmaceutical composition according to the invention for the preparation of pharmaceutical solutions and in particular solutions for injection or infusion. Such solutions are usually prepared by dissolving the crystalline form B, the treosulfan or the pharmaceutical composition in a solvent, such as solvent commonly employed for reconstitution.

The invention is explained in more detail below with reference to non-limiting examples which also include methods which are in particular suitable to determine the above-mentioned properties of the crystalline form B and the treosulfan according to the invention.

EXAMPLES

Methods

The following methods have been used for obtaining X-ray powder diffraction (XRPD) patterns, for investigations by means of single-crystal x-ray diffraction (SCXRD) and optical microscopy, for determining the amount of crystalline form B and crystalline form A and the amount of amorphous phase, and for determining the amount of treosulfan, methanesulfonic acid and water.

X-Ray Powder Diffraction (XRPD)

The respective sample was introduced in a standard glass capillary (Ø=0.7 mm) after careful manual grinding with a pestle in a mortar. The X-ray powder diffraction pattern was recorded at room temperature using a Bruker D8 Advance Diffractometer (Cu-K$\alpha$1=1.54059 Å, Johansson primary beam monochromator, position sensitive detector) in transmission mode with rotation of the sample. Data were collected in the range of 3 to 50 degrees 2Θ. The tube voltage and current were set to 40 kV and 40 mA, respectively.

Single-Crystal x-Ray Diffraction (SCXRD)

Single crystal X-ray diffraction data were recorded using a "Rigaku Xcalibur, Sapphire2, large Be window" diffractometer equipped with an X-ray generator containing a molybdenum anode (Mo-K$\alpha$=0.71073 Å).

Determination of Amount of Form B and A by XRPD and Rietveld Analysis

For determining the amount of crystalline form B and A of treosulfan, a respective sample was introduced in a standard glass capillary (Ø=0.7 mm) after careful manual grinding with a pestle in a mortar. The x-ray powder diffraction pattern was recorded at room temperature using a Bruker D8 Advance diffractometer (Cu-K$\alpha$1=1.54059 Å, Johansson primary beam monochromator, position sensitive detector) in transmission mode with rotation of the sample. Data were collected in the range of 4 to 50 degrees 2Θ over a period of 4 h. The tube voltage and current were set to 40 kV and 40 mA, respectively. The obtained data were subjected to a quantitative Rietveld analysis by means of the TOPAS software.

Determination of Amount of Amorphous Phase by XRPD and Rietveld Analysis with Internal Standard For determining the amount of amorphous phase, a respective sample was mixed with 25% by weight of $CaF_2$ (Aldrich Chemistry, Lot #MKBP1959V, Calcium Fluoride anhydrous, 99.99%) as internal standard. After careful manual grinding with a pestle in a mortar, the mixture was introduced in a standard glass capillary (Ø=1.0 mm). The x-ray powder diffraction pattern was recorded at room temperature using a Bruker D8 Advance diffractometer (Cu-K$\alpha$1=1.54059 Å, Johansson primary beam monochromator, position sensitive detector) in transmission mode with rotation of the sample. Data were collected in the range of 4 to 50 degrees 2Θ over a period of 12 h. The tube voltage and current were set to 30 kV and 30 mA, respectively. The obtained data were subjected to a quantitative Rietveld analysis by means of the TOPAS software.

Crystalline form A and crystalline form B were the only crystalline phases which could be identified.

Optical Microscopy

The investigations were performed using a Leica DMRB microscope equipped with a camera system from Kappa, type ZELOS. Samples were examined in purified silicon oil on a purified tray and images were taken with polarized light and lambda slip for higher color contrast.

Determination of Amount of Treosulfan by RP-HPLC

The amount of treosulfan in a respective sample was determined using reversed-phase high pressure liquid chromatography (RP-HPLC) as indicated in the following:

| HPLC Equipment | Agilent Technologies |
|---|---|
| Column | Luna C18(2), 5 µm, 250 × 4.6 mm (phenomenex) |
| Mobile phase A | 720 ml diluent + 30 ml methanol Isocratic, 25 min |
| Flow rate | 0.8 ml/min |
| Column temperature | 40° C. |
| Injected volume | 20 µl |
| Diluent | 697 mg $K_2HPO_4$/1000 ml, pH 4.5 ($H_3PO_4$) |
| Detection | Refractive index detector |
| Reference solution | 50 mg/ml treosulfan in diluent |
| Sample Solution | 50 mg/ml treosulfan in solvent for reconstitution |

Determination of Amount of Methanesulfonic Acid by HILIC

The amount of methanesulfonic acid (MSA) was determined using Hydrophilic Interaction Liquid Chromatography (HILIC) as indicated in the following:

| HPLC Equipment | |
|---|---|
| Column | Nucleodur HILIC (250 × 4.6 mm, 3 µm) |
| Eluent | 10 mmol Ammonium formiate in $H_2O$/acetonitrile (7:93)(Vol/Vol) |
| Flow rate | 1.4 ml/min |
| Column temperature | 45° C. |
| Injected volume | 20 µl |
| Detector | 35° C. |
| Run time | 1.5 times the retention time of methanesulfonic acid |
| Detection | Refractive index detector |
| Reference solution 1 | Dissolve methanesulfonic acid in HPLC-grade water to a final concentration of 2.0 mg/ml |
| Reference solution 2 | Dilute reference solution 1 with eluent to 0.1 mg/ml. Reference solution 2 is used for quantification of methanesulfonic acid in the test solution. |
| Test solution | Dissolve sample to be tested in HPLC-grade water to a final concentration of 20 mg/ml |

Determination of Amount of Water by "Karl Fischer Titration"

About 100 mg of the respective sample was weighed into a glass vial which was sealed with a crimp cap. The sample was transferred into the furnace of a Karl Fischer coulometer type 756, furnace sample processor 774, of Metrohm (Filderstadt, Germany) which was heated to 90° C. The septum of the cap was penetrated by an injection needle, and the generated water vapour was directly transferred into the titration chamber of the Karl Fischer coulometer via dry nitrogen. The measurement was repeated once. Empty glass vials were used for blank correction.

Example 1—Preparation of Form B Using Water/Isopropanol 99.8 mg treosulfan were weighed in a vial (volume 4.0 ml) which was equipped with a PTFE (Polytetrafluoroethylene) sealing and a stirrer. 1.5 ml of a mixture of 80% by weight water and 20% by weight isopropanol preheated to 65° C. were then added. The resulting solution was completely taken up with a syringe (volume 5 ml) and filtered using a 0.2 µm filter into a second vial (volume 4.0 ml). The syringe, second vial and filter had been tempered at 65° C. before use. The solvents were allowed to evaporate from the open vial at room temperature to dryness which resulted in formation of crystals.

The XRPD pattern of the obtained crystals of form B according to the invention is shown in FIG. 1.

Example 2—Preparation of Form B Using 1,4-Dioxane 20.1 mg treosulfan were weighed in a vial (volume 4.0 ml) which was equipped with a PTFE (Polytetrafluoroethylene) sealing and a stirrer. 185 µl of 1,4-dioxane were added at room temperature. After complete dissolution of the solid, the sealing was removed and the solvent was allowed to evaporate to dryness at room temperature.

The crystals obtained were analyzed by XRPD which showed them to be crystalline form B according to the invention.

Example 3—Preparation of Form B Using Methyl Isobutyl Ketone 19.7 mg treosulfan were weighed in a vial (volume 4.0 ml) which was equipped with a PTFE (Polytetrafluoroethylene) sealing and a stirrer. 2.5 ml methyl isobutyl ketone (MIBK) were added at room temperature. After complete dissolution of the solid, the solution was completely taken up with a syringe (volume 5 ml) and filtered using a 0.2 µm filter into a second vial (volume 4.0 ml). The solvent was then allowed to evaporate from the open vial to dryness at room temperature.

The crystals obtained were analyzed by XRPD which showed them to be crystalline form B according to the invention.

Example 4—Preparation of Form B Using Ethyl Acetate 20.0 mg treosulfan were weighed in a vial (volume 4.0 ml) which was equipped with a PTFE (Polytetrafluoroethylene) sealing and a stirrer. 2.0 ml ethyl acetate were added at room temperature. After complete dissolution of the solid, the solution was completely taken up with a syringe (volume 5 ml) and filtered using a 0.2 µm filter into a second vial (volume 4.0 ml). The solvent was then allowed to evaporate from the open vial to dryness at room temperature.

The crystals obtained were analyzed by XRPD which showed them to be crystalline form B according to the invention.

Example 5—Preparation of Form B Using Tetrahydrofuran 50.0 mg treosulfan were weighed in a vial (volume 4.0 ml) which was equipped with a PTFE (Polytetrafluoroethylene) sealing and a stirrer. 0.85 ml tetrahydrofuran (THF) were added at room temperature. After complete dissolution of the solid, the solution was completely taken up with a syringe (volume 5 ml) and filtered using a 0.2 µm filter into a second vial (volume 5.0 ml) which contained 2.85 ml methyl tert-butyl ether (MTBE). The second vial was then carefully shaken which quickly resulted in formation of crystals which were separated by filtration.

The crystals obtained were analyzed by XRPD which showed them to be crystalline form B according to the invention.

Example 6—Preparation of Form B Using Methyl Ethyl Ketone 50.1 mg treosulfan were weighed in a vial (volume 4.0 ml) which was equipped with a PTFE (Polytetrafluoroethylene) sealing and a stirrer. 1.1 ml methyl ethyl ketone (MEK) were added at room temperature. After complete dissolution of the solid, the solution was completely taken up with a syringe (volume 5 ml) and filtered using a 0.2 µm filter into a second vial (volume 5.0 ml) which contained 3.3 ml methyl tert-butyl ether (MTBE) while stirring. This resulted in immediate formation of crystals which were separated by filtration.

The crystals obtained were analyzed by XRPD which showed them to be crystalline form B according to the invention.

The crystals were moreover investigated by optical microscopy and a corresponding photomicrograph is shown in FIG. 2.

Example 7—SCXRD Analysis of Form B

A suitable single-crystal of form B was selected under the microscope from the crystals obtained in accordance with example 3 and was analyzed by means of single-crystal X-ray diffraction (SCXRD). The obtained data are represented above in the section preceding the examples.

Example 8—Preparation of Crystalline Form A (Reference)

About 5 g treosulfan were dissolved in about 80 g of 2-propanol under stirring at 65° C. The resulting solution was then filtered using a 0.2 µm filter and cooled to 15° C. which resulted in the precipitation of crystals. The crystals were collected and dried at about 40° C.

Figure 3:
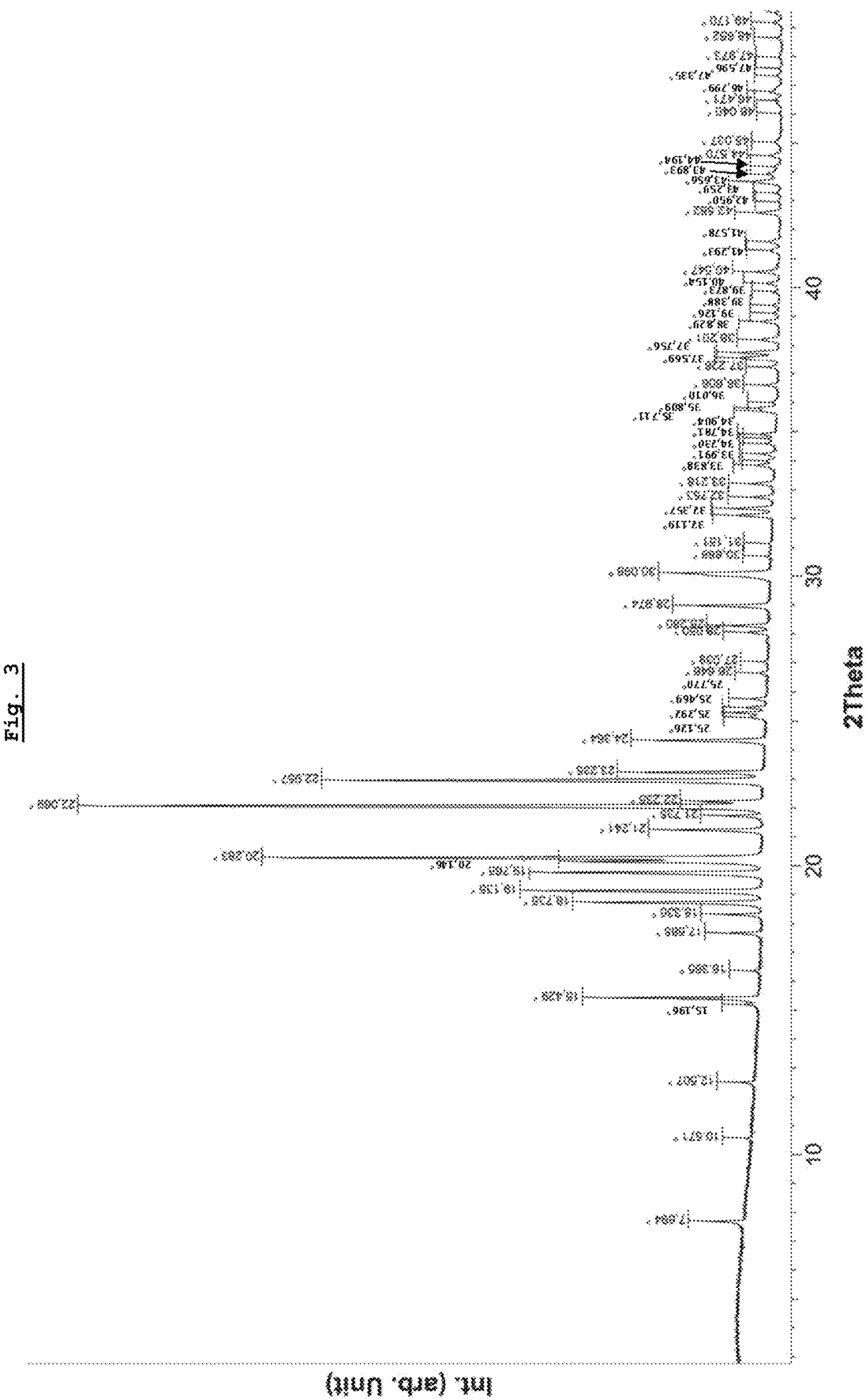
FIG. 3 shows an XRPD pattern of crystals of crystalline form A of treosulfan.

The XRPD pattern of the dried crystals is shown in FIG. 3 and confirms it to be crystalline form A of treosulfan. The crystalline form A exhibits an XRPD pattern having characteristic peaks at 7.69, 15.43, 18.74, 19.14, 19.77, 20.15, 20.28, 21.24, 21.74, 22.07, 22.96, 23.24, 24.36, 25.29, 28.05, 28.28, 28.97, 30.10 and 40.55±0.20 degrees 2Θ.

The dried crystals were moreover investigated by optical microscopy and a corresponding photomicrograph is shown in FIG. 4.

In addition, a suitable single-crystal of form A was selected under the microscope and was analyzed by means of single-crystal X-ray diffraction (SCXRD). The obtained data are presented above in the section preceding the examples.

Example 9—Preparation of Lyophilisate of Crystalline Form B

The pre-lyophilization solution of the composition as given in the table below was prepared by weighing water into a glass beaker and adjusting its temperature to 30° C. using a water bath. The corresponding amount of treosulfan was added and the mixture was stirred at 30° C. for 30 min. The obtained solution was filtered and the filtered solution was immediately filled into cleaned and depyrogenized glass vials which were tempered at 30° C.

Composition of Pre-Lyophilization Solution, Target Dose about 5000 mg Treosulfan Per Vial

| Concentration of treosulfan | Solvent | Fill per vial |
|---|---|---|
| 80 mg/g | Water for injection | 62.5 g |

The vials were stoppered in lyophilisation position and sealed in lyophilization bags. The samples were loaded into a freeze dryer GT 2 (Manufacturer: Hof Sonderanlagenbau (Lohra, Germany)) with 0.4 m² shelf area and 8 kg ice condenser capacity including means for differential pressure measurement and lyophilized according to the following lyophilization cycle.

Lyophilization Cycle

| # | Step Description | Shelf temperature [° C.] | Ice condenser temperature [° C.] | Pressure [mbar] | Time step [h:min] | Cumulative time [h:min] |
|---|---|---|---|---|---|---|
| 1 | Loading | 30 | — | 1000 | 00:01 | 00:01 |
| 2 | Freezing ramp (1.17 K/min) | −45 | — | 1000 | 01:04 | 01:05 |
| 3 | Freezing | −45 | — | 1000 | 06:00 | 07:05 |
| 4 | Annealing ramp (1 K/min) | −10 | — | 1000 | 00:35 | 07:40 |
| 5 | Annealing | −10 | — | 1000 | 06:00 | 13:40 |
| 6 | Freezing ramp (1 K/min) | −45 | — | 1000 | 00:35 | 14:15 |
| 7 | Freezing | −45 | — | 1000 | 03:00 | 17:15 |

-continued

| # | Step Description | Shelf temperature [° C.] | Ice condenser temperature [° C.] | Pressure [mbar] | Time step [h:min] | Cumulative time [h:min] |
|---|---|---|---|---|---|---|
| 8 | Vacuum adjustment | −45 | ≤−70 | 0.33 | 00:30 | 17:45 |
| 9 | Primary Drying ramp (0.94 K/min) | 35 | ≤−70 | 0.33 | 01:25 | 19:10 |
| 10 | Primary Drying | 35 | ≤−70 | 0.33 | 62:00 | 81:10 |

The obtained lyophilisate cakes were homogenous without any defects. For reconstitution testing, the vials were vented, opened and 100 ml of 0.45% by weight aqueous NaCl solution (room temperature) were added to give a final concentration of treosulfan of 50 mg/ml. The lyophilisate cakes reconstituted within 30 seconds only. No pre-heating of the solvent was necessary. The removal of sticky particles adhering to the wall of the vials was also not necessary.

All lyophilisates showed a very low amount of residual water and a very low amount of methanesulfonic acid. The latter was even below the limit of detection (LOD) of 0.01% by weight.

Properties of Lyophilisates

| Amount of treosulfan [% by weight] | Amount of water [% by weight] | Amount of methanesulfonic acid [% by weight] | Reconstitution time |
|---|---|---|---|
| 101.79 | 0.01 | <LOD | 30 s |

The lyophilisates obtained were also subjected to XRPD analyses using Rietveld refinement to determine their crystallinity as well as their amount of form A, form B and amorphous phase. Crystalline form A and B were the only crystalline phases which could be detected. The results are given in the following table.

Results of XRPD Analyses

| Amount of crystalline treosulfan [% by weight] | Amount of form A and B [% by weight] | | Amount of amorphous phase [% by weight] |
|---|---|---|---|
| | Form A | Form B | |
| 96.3 | 0.5 | 99.5 | 3.7 |

Figure 5:
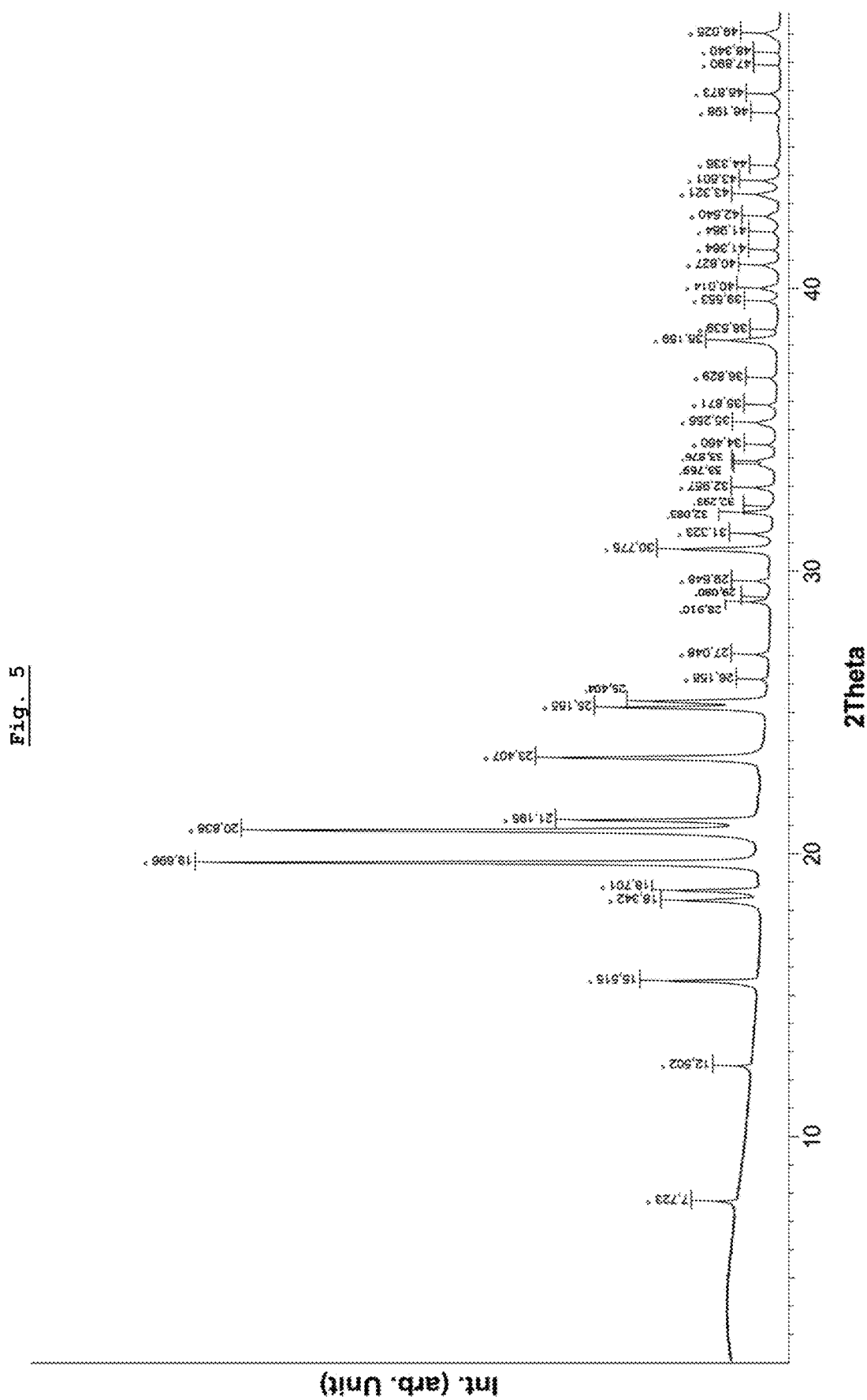
FIG. 5 shows an XRPD pattern of a lyophilisate of crystalline form B of treosulfan.

The XRPD pattern of the lyophilisates is shown in FIG. 5.

The invention claimed is:

1. A crystalline form B of treosulfan, which exhibits an X-ray powder diffraction pattern having characteristic peaks at 20.87 and 23.47±0.20 degrees 2Θ.

2. The crystalline form B according to claim 1, which exhibits an X-ray powder diffraction pattern having characteristic peaks at 20.87, 23.47, 26.20, 29.65, 30.81, 34.54, 35.30, 36.87 and 46.24±0.20 degrees 2Θ.

3. The crystalline form B according to claim 1, which exhibits an X-ray powder diffraction pattern essentially as shown in FIG. 1.

4. The crystalline form B according to claim 1, which exhibits an X-ray powder diffraction pattern having no peaks in at least one of the following regions a to f, expressed as degrees 2Θ:

| Region | Degrees 2Θ |
|---|---|
| a | 19.00-19.50 |
| b | 20.00-20.65 |
| c | 21.50-23.21 |
| d | 23.75-24.95 |
| e | 27.40-28.35 |
| f | 30.00-30.60. |

5. A treosulfan which comprises at least 96% by weight of the crystalline form B according to claim 1, relative to the combined amount of the crystalline form B and a crystalline form A.

6. A treosulfan which comprises at least 75% by weight of the crystalline form B according to claim 1, relative to the amount of treosulfan.

7. The treosulfan according to claim 5, which comprises less than 20% by weight of amorphous phase.

8. The treosulfan according to claim 5, which comprises less than 0.2% by weight of methanesulfonic acid.

9. A process for preparing the crystalline form B according to claim 1, which process comprises
(A) recrystallizing treosulfan from organic solvent, optionally comprising water, or
(B) dissolving treosulfan in organic solvent, optionally comprising water, and allowing evaporation of solvent and optional water to dryness, or
(C) dissolving treosulfan in organic solvent, optionally comprising water, and adding anti-solvent.

10. The process according to claim 9, wherein the organic solvent in variant (A), variant (B) and variant (C) is selected from the group of ethers, ketones, esters and alcohols or mixtures thereof.

11. The process according to claim 9, wherein in variant (B) a mixture of water and isopropanol is used and water and isopropanol are allowed to evaporate to dryness at room temperature.

12. The process according to claim 11, wherein the mixture comprises about 80% by weight of water and about 20% by weight of isopropanol.

13. The process according to claim 9, wherein in variant (C) the anti-solvent is selected from methyl tert-butyl ether, toluene, hexane, pentane, chloroform, and methylene chloride.

14. A pharmaceutical composition comprising the crystalline form B according to claim 1 and optionally at least one pharmaceutically acceptable additive.

15. The pharmaceutical composition according to claim 14, which is in the form of a powder, a tablet, granules or a capsule.

16. A method of treating cancer comprising administering the crystalline form B of treosulfan according to claim 1 to a patient suffering from cancer.

17. A method comprising administering the crystalline form B of treosulfan according to claim 1 to a patient as conditioning therapy before transplantation of bone marrow or of blood stem cells to the patient.

18. A method of treating cancer, the method comprising preparing a solution for injection or infusion from the crystalline form B of treosulfan according to claim 1 and administering said solution to a patient suffering from cancer.

19. A method comprising preparing a solution for injection or infusion from the crystalline form B of treosulfan according to claim 1 and administering said solution to a patient as conditioning therapy before transplantation of bone marrow or of blood stem cells to the patient.

\* \* \* \* \*